United States Patent [19]

Hayasaka et al.

[11] 4,410,716

[45] Oct. 18, 1983

[54] DIBENZO[a,d]CYCLOHEPTENE DERIVATIVES AND PROCESS FOR PRODUCTION THEREOF

[75] Inventors: Tetsutaro Hayasaka; Kuniro Saito; Sen-ichi Narita, all of Fukushima; Takao Goto, Koori; Shin-ichi Yamada, Fukushima; Teruo Saito, Date; Kazuyoshi Okutani, Fukushima, all of Japan

[73] Assignee: Toa Eiyo Kagaku Kogyo Co. Ltd., Tokyo, Japan

[21] Appl. No.: 190,270

[22] Filed: Sep. 24, 1980

[30] Foreign Application Priority Data

Sep. 29, 1979 [JP] Japan .................. 54-124741

[51] Int. Cl.$^3$ .......................................... C07C 69/76
[52] U.S. Cl. .................................. 560/51; 560/56; 560/52; 560/50; 562/461; 562/466; 562/460; 562/488; 562/459; 424/308; 260/410.9 R; 260/465 H; 568/308; 568/325; 568/807
[58] Field of Search ................ 560/56, 51; 562/461, 562/466

[56] References Cited

U.S. PATENT DOCUMENTS

| | | | |
|---|---|---|---|
| 3,933,905 | 1/1976 | Brunet et al. | 560/53 |
| 3,966,820 | 6/1976 | Nelson et al. | 560/51 |
| 3,975,437 | 8/1976 | Brunet et al. | 560/53 |

*Primary Examiner*—Paul J. Killos
*Attorney, Agent, or Firm*—Sherman & Shalloway

[57] ABSTRACT

Novel compounds, dibenzo[a,d]cycloheptene derivatives, of the general formula $$R_1 \text{—[ring system]—} CHCOOR_3 \quad (I)$$
with $R_2$ and $Z$ wherein $R_1$ represents a hydrogen atom, a halogen atom or a lower alkyl group, $R_2$ and $R_3$ each represent a hydrogen atom or a lower alkyl group, and Z represents a group of the formula $$-\underset{OR_3}{\overset{|}{C}}=CH- \quad \text{or} \quad -\underset{O}{\overset{||}{C}}-CH_2-.$$

These novel compounds are useful as non-steroidal anti-inflammatory agents free from gastrointestinal lesions. The compounds of formula (I) can be prepared, for example, by cyclizing a compound of the general formula $$R_1\text{—[ring system]—}CHCOX \quad (II)$$
with Y Y' and $R_2$ wherein $R_1$ and $R_2$ are as defined above, X represents a hydroxyl group or a halogen atom, one Y represents a group of the formula —$CH_2COX$ and the other Y represents a hydrogen atom; optionally hydrolyzing the cyclized product; and optionally esterifying the product, and/or etherifying its enol group.

12 Claims, No Drawings

DIBENZO[a,d] CYCLOHEPTENE DERIVATIVES AND PROCESS FOR PRODUCTION THEREOF

This invention relates to novel dibenzo[a,d]cycloheptene derivatives of the general formula

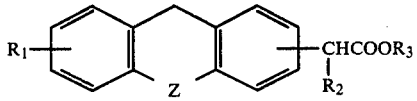
(I)

wherein $R_1$ represents a hydrogen atom, a halogen atom or a lower alkyl group, $R_2$ and $R_3$ each represent a hydrogen atom or a lower alkyl group, and Z represents a group of the formula

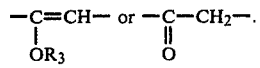

Many non-steroidal anti-inflammatory agents have been known in the past, but they cause side-effects such as gastrointestinal lesions.

It is an object of this invention therefore to provide non-steroidal anti-inflammatory agents free from such defects.

We have now found that the novel dibenzo[a,d]cycloheptene derivatives of general formula (I) have strong anti-inflammatory activity with very little gastrointestinal lesions.

The novel compound of general formula (I) can be prepared by cyclizing a compound of the general formula

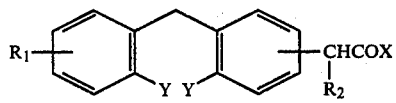
(II)

wherein $R_1$ and $R_2$ are as defined above, X represents a hydroxyl group or a halogen atom, one Y represents a group of the formula —$CH_2COX$ and the other Y represents a hydrogen atom,
optionally hydrolyzing the cyclized product, and thereafter optionally esterifying it, and/or etherifying its enol group.

The compound of formula (II) is also a novel compound and can be produced by reducing the carbonyl group of a compound of the general formula

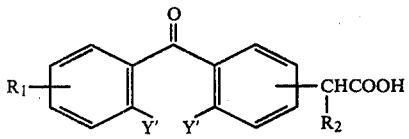
(III)

wherein $R_1$ and $R_2$ are as defined, and one Y' represents a group of the formula —$CH_2COOH$ and the other Y' represents a hydrogen atom,
to a methylene group, and optionally halogenating the resulting product.

The compound of general formula (III) can be produced, for example, by the following method.

For example, a compound of the general formula

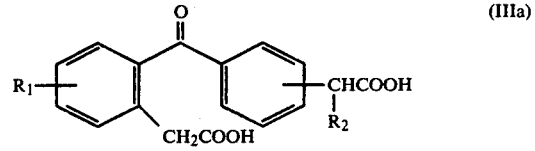
(IIIa)

wherein $R_1$ and $R_2$ are as defined above, can be produced by heating a compound of the general formula

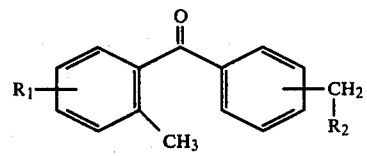

wherein $R_1$ and $R_2$ are as defined above, under reflux in benzene together with ethylene glycol in the presence of an acid to form a ketal compound of the general formula

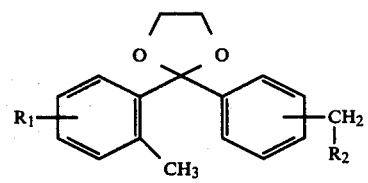

wherein $R_1$ and $R_2$ are as defined above, brominating the resulting compound by the action of N-bromosuccinimide in carbon tetrachloride, treating the product with sodium cyanide or potassium cyanide in a mixture of ethanol and water to form a compound of the general formula

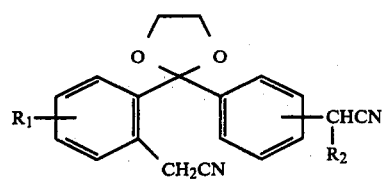

wherein $R_1$ and $R_2$ are as defined above, hydrolyzing the resulting compound in a sodium hydroxide solution, deketalizing the compound in a mixture of hydrochloric acid and ethanol to form a compound of the general formula

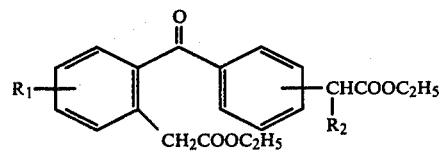

wherein $R_1$ and $R_2$ are as defined hereinabove and hydrolyzing the product in a sodium hydroxide solution.

Likewise, a compound of the general formula

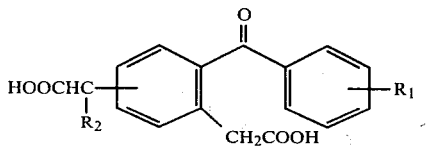

(IIIb)

wherein $R_1$ and $R_2$ are as defined above,
can be produced from a compound of the general formula

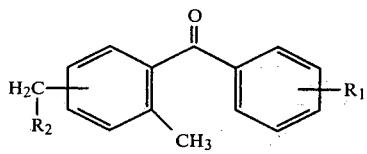

wherein $R_1$ and $R_2$ are as defined above.

In the production of the compound (I) from the compound (III), the carbonyl group of the compound (III) is reduced to a methylene group by the action of a reducing agent, and optionally hydrolyzing the product and halogenating the carboxyl group to form the compound of formula (II).

Reduction of the carbonyl group is performed by using such a reducing agent as zinc powder, a powder of a zinc-copper alloy, red phosphorus, or zinc amalgam. The reaction is carried out preferably in a solvent. When zinc powder, or a powder of zinc-copper alloy is used as the reducing agent, a 5–30% basic aqueous solution is preferred as the solvent. Examples of the base are sodium hydroxide, potassium hydroxide or ammonia. The reaction temperature is usually 50° to 110° C. When zinc amalgam is used as the reducing agent, an aqueous solvent acidified with hydrochloric acid is preferred as the solvent. The aqueous solvent may, for example, be water, hydrous methanol, hydrous ethanol, hydrous propanol, or mixtures of these. The reaction proceeds smoothly at a temperature of 50° to 100° C.

Subsequently, the partially esterified product is hydrolyzed in a customary manner with a base such as sodium hydroxide or potassium hydroxide in a solvent, preferably such as a mixture of ethanol and water.

Of the compounds falling within the general formula (II), a 2-(4-substituted benzyl)phenylacetic acid derivative of the general formula

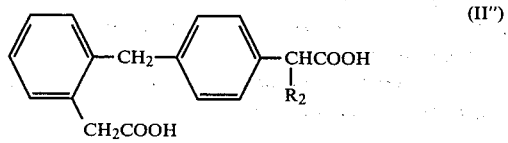

(II″)

wherein $R_2$ is as defined hereinabove,
can be produced by reducing a compound of the general formula

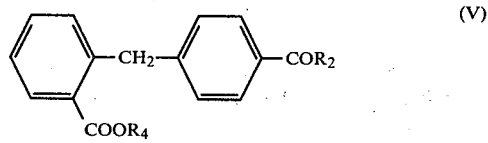

(V)

wherein $R_2$ is as defined above, and $R_4$ represents a hydrogen atom or a lower alkyl group,
to form an alcohol compound of the general formula

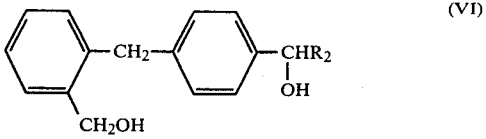

(VI)

wherein $R_2$ is as defined above,
halogenating the alcohol compound and then treating it with a cyanide, and hydrolyzing the product of the general formula

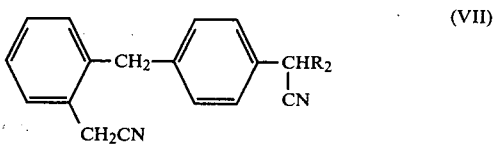

(VII)

wherein $R_2$ is as defined above.

The compound of formula (V) is obtained, for example, by reacting ethyl 2-benzylbenzoate with acetyl chloride, acetic anhydride or α,α-dichloromethyl methyl ether in the presence of anhydrous aluminum chloride or stannic chloride.

Reduction of the compound of formula (V) is carried out in a solvent using a reducing agent. Examples of preferred reducing agents are lithium aluminum hydride, sodium borohydride-aluminum chloride, and sodium bis(2-methoxyethoxy)aluminum hydride. The solvent may, for example, be ether, tetrahydrofuran, diglyme, benzene, toluene, or mixtures thereof. The reaction temperature is from room temperature to the boiling point of the solvent.

The resulting alcohol compound (VI) is halogenated in a customary manner and then treated with a cyanide to form the product of formula (VII). The halogenation is carried out at 0° to 150° C. using an ordinary halogenating agent such as thionyl chloride, phosphorus tribromide, phosphorus pentachloride or phosphorus oxychloride in the absence of a solvent or in the presence of an inert solvent such as benzene, carbon tetrachloride, 1,2-dichloroethane or chloroform. The cyanation is carried out in an inert solvent using a cyanation agent such as potassium cyanide or sodium cyanide. Examples of the solvent are hydrous ethanol, dimethyl formamide, dimethyl acetamide, dimethyl sulfoxide, sulfolane, and hexamethylphosphoramide. Addition of a quaternary salt of an amine, such as tetrabutyl ammonium chloride or benzyl triethyl ammonium chloride, promotes the cyanation.

Hydrolysis of the product (VII) is carried out in a customary manner, for example, by heating the compound in hydrous alcohol in the presence of a base such as sodium hydroxide or potassium hydroxide.

The 2-(4-substituted benzyl)phenylacetic acid derivatives of formula (II″) can also be prepared by reacting a compound of the general formula

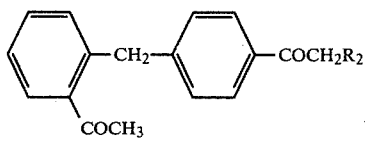

wherein $R_2$ is as defined above,
with a lower alcohol in the presence of a thallium (III) salt, and optionally hydrolyzing the product (ester).

The compound of formula (VIII) is also a novel compound, and can be prepared, for example, by the action of an acid chloride or acid anhydride on o-benzylacetophenone in the presence of anhydrous aluminum chloride.

Methanol, ethanol, propanol, butanol, etc. can be used as the lower alcohol. Thallium trinitrate is preferred as the thallium (III) salt, and thallium trinitrate supported on acidic montmorillonite is especially preferred.

This reaction is preferably carried out in the presence of an acid catalyst. Examples of preferred acid catalysts are mineral acids such as perchloric acid, nitric acid or hydrochloric acid. The reaction may be carried out in the absence of a solvent or in the presence of an inert solvent. Examples of the inert solvent are methylene chloride, carbon tetrachloride, toluene and mixtures of these. The reaction temperature is usually room temperature to the boiling point of the reaction mixture. Generally, the reaction is completed in 1 to 40 hours.

Use of thallium trinitrate as the thallium (III) salt supported on acidic montmorillonite, for example K-10 (a product of Sued Chemie Companh), promotes the reaction, and the reaction time can be shortened to from 0.5 to 2 hours. Thallium trinitrate can be supported on a carrier by a method described, for example, in Journal of the American Chemical Society, Vol. 98, page 6750, 1971. In this case, thallium trinitrate and methanol adsorbed to the surface of the acidic montmorillonite serve as reagents.

Hydrolysis of the ester of the general formula

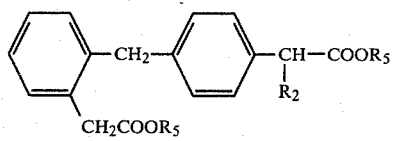

wherein $R_2$ is as defined above, and $R_5$ represents a lower alkyl group,
can be performed by known means using a mineral acid such as hydrochloric acid or sulfuric acid or an alkali such as sodium hydroxide or potassium hydroxide.

A compound of general formula (II) in which X is halogen can be produced by halogenating the carboxyl group of the compound so obtained at 0° to 150° C. with an ordinary halogenating agent such as thionyl chloride, phosphorus tribromide, phosphorus pentachloride or phosphorus oxychloride in the absence of a solvent or in the presence of an inert solvent such as benzene, toluene, xylene, ether, chloroform or dichloroethane. or dichloroethane.

Cyclization of the compound of formula (II) may be carried out in the presence of a condensing agent such as polyphosphoric acid, polyphosphoric acid esters or phosphoric anhydride when X is a hydroxyl group, and in the presence of a Friedel-Crafts reaction catalyst such as aluminum chloride, zinc chloride, stannous chloride, stannic chloride, titanium trichloride, boron trifluoride, antimony pentachloride or phosphoric anhydride when X is a halogen atom.

When X is a hydroxyl group, the cyclization reaction does not particularly require a solvent, but the use of benzene, xylene, acetic acid, dimethyl sulfoxide, sulfolane, etc. as a solvent is permissible. The reaction temperature is usually from room temperature to 150° C. When X is a halogen atom, it is preferred to use an inert solvent such as nitrobenzene, nitromethane, dichloromethane, dichloroethane or carbon disulfide. The reaction proceeds smoothly at −30° to +100° C.

According to a preferred embodiment of this invention, the compound of this invention is produced by cyclizing a compound of the general formula

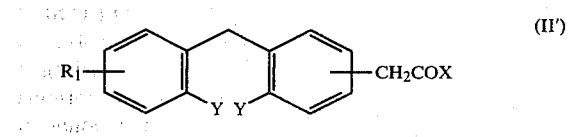

wherein $R_1$, X and Y are as defined above,
optionally hydrolyzing the cyclized product to form a compound of the general formula

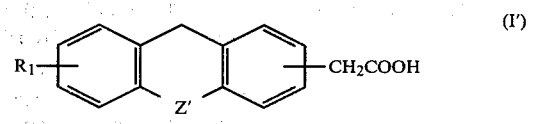

wherein $R_1$ is as defined above, and $Z'$ represents a group of the formula

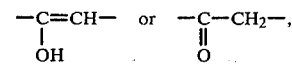

esterifying and enol-etherifying the compound, and thereafter optionally subjecting the resulting compound of the general formula

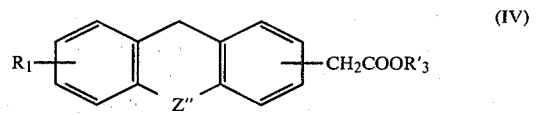

wherein $R_1$ is as defined above, $R'_3$ represents a lower alkyl group, and $Z''$ represents a group of the formula

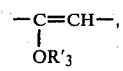

to alkylation, dealkylation of the enol ether group, and/or hydrolysis.

Cyclization of the compound of formula (II') can be performed by the method described hereinabove.

To esterify and enol-etherify the compound of formula (I') simultaneously, the compound of formula (I') is reacted with a lower alcohol in the presence of, for example, thionyl chloride, phosphorus pentachloride, phosphorus tribromide, phosphorus oxychloride, etc. Examples of the lower alcohol are methanol, ethanol, n-propanol, isopropanol, and n-butanol. There can be used a solvent, for example the aforesaid lower alcohols, and inert solvents such as benzene, toluene, xylene, n-hexane, ether, tetrahydrofuran, chloroform, and dichloromethane. The reaction temperature is usually from room temperature to 120° C.

The compound of formula (IV) may also be obtained by esterifying the compound of formula (I') and then subjecting it to the aforesaid reaction. The esterification reaction of the compound of formula (I') is carried out using a lower alcohol in the presence of an ordinary inorganic acid such as hydrogen chloride, hydrogen bromide or sulfuric acid. The aforesaid lower alcohols, and inert solvents such as benzene, toluene, xylene or mixtures thereof may be used as a reaction solvent. The reaction temperature is preferably 60° to 120° C.

When the compound of formula (IV) is subjected to dealkylation of the enol ether group or to hydrolysis, a compound of formula (I) in which $R_2$ is a hydrogen atom can be obtained. To obtain a compound of formula (I) in which $R_2$ is a lower alkyl group, the compound of formula (IV) is alkylated, for example, in the following manner.

The compound of formula (IV) is reacted with an alkyl halide in the presence of a base in a dry solvent. Examples of the base are lithium alkyl amides, lithium amide, n-butyl lithium, phenyl lithium, sodium hydride or sodium amide. Examples of the solvent are inert solvents such as ether, tetrahydrofuran, dimethoxyethane, diglyme, dioxane, benzene, toluene, hexane, dimethyl formamide, dimethyl acetamide, hexamethylphosphoramide, and liquid ammonia. Preferably, the reaction is carried out in a stream of an inert gas such as nitrogen. The reaction temperature is usually $-60°$ to $+100°$ C.

When the resulting compound is hydrolyzed in the presence of a base or an acid, a compound of formula (I) in which $R_3$ is a hydrogen atom can be obtained in a high yield. The base may, for example, be sodium hydroxide, potassium hydroxide, etc., and the acid may, for example, be hydrochloric acid, hydrobromic acid, etc. Usually, water or a mixture of water and a lower alcohol is used as a solvent. It may be used in admixture with an organic solvent such as benzene, toluene or hexane. The reaction proceeds smoothly at room temperature to 130° C.

The compound of formula (I) in which $R_3$ is a hydrogen atom can also be produced by dealkylating the enol ether group of the alkylated product, and then hydrolyzing the resulting product by the method described above. Dealkylation of the enol ether group is carried out in the presence of a protonic acid or a Lewis acid. When a protonic acid such as hydrochloric acid or hydrobromic acid is used, the reaction temperature is preferably 0° to 30° C. The reaction usually proceeds smoothly in water, a lower alcohol or a mixture of these. An organic solvent such as benzene, hexane and ether may also be used in admixture. When a Lewis acid such as boron tribromide or boron trichloride is used, the reaction temperature is preferably from $-30°$ C. to 0° C. The reaction is preferably carried out in an organic solvent such as hexane, chloroform, and dichloromethane.

The final desired products can be isolated and purified in a customary manner by, for example, extraction, recrystalization, chromatography, etc. in suitable combinations.

The anti-inflammatory activity, analgesic activity and ulcerogenic activity of the novel dibenzo[a,d]cycloheptene derivatives of this invention were tested by the following methods.

(A) Anti-inflammatory activity

Each of test compounds was orally administered to groups of male Donryu rats weighing 130 to 150 g (8 to 10 rats per group), and one hour later, 0.1 ml of a 1% carrageenin solution was injected subcutaneously into the hind paw of each rat. After injection of carrageenin, the volume of the paw was measured at predetermined periods, and the percent inhibition against a control group was calculated. The results are shown in Table 1. It is seen from Table 1 that the dibenzo[a,d]cycloheptene derivatives Ia, Ib, Ic, Ih and Ii exhibited excellent anti-inflammatory activity, and in particular, the efficacy of the compound Ii was stronger than that of indomethacin as a comparison.

(B) Analgesic activity

Using male ICR mice weighing 25 to 30 g (10 mice per group), there was measured the number of writhing syndromes induced when a 1% solution of acetic acid was intraperitoneally injected at a dose of 10 ml/kg. The percent inhibition against a control group was calculated. The results are shown in Table 2. It is seen from Table 2 that the $ED_{50}$ value (52 mg/kg) of the compound Ii was ten times that (5.0 mg/kt) of indomethacin, and, therefore, the analgesic activity of the compound Ii is one-tenth of that of indomethacin.

(C) Ulcerogenic activity

Each of the test compounds was orally administered to male Donryu rats weighing 150 to 170 g which had been caused to fast for 9 hours. Sixteen hours later, the rats were sacrificed under ether anesthesia. The stomach was removed from each rat, and the number of animals which showed hemorrhagic and/or ulcerous spots in the gastric wall was calculated. The results are shown in Table 3. It is seen from Table 3 that the compound Ii scarcely caused gastric lesions even in doses which would evidently exhibit anti-inflammatory activity. The $UD_{50}$ value (15 mg/kg) of the compound Ii was 7.9 times the $ED_{40}$ value (1.9 mg/kg) of its anti-inflammatory activity. On the other hand, the $UD_{50}$ value (11.7 mg/kg) of indomethacin was only 1.2 times the $ED_{40}$ value (9.8 mg/kg) of its anti-inflammatory acticity.

The results of these tests demonstrate that the compound Ii is a useful anti-inflammatory agent which has very potent anti-inflammatory activity and weak analgesic activity, but its ulcerogenic activity is extremely weak. It is also seen that the compounds Ia, Ib, Ic and Ih evidently show anti-inflammatory activity although their activity is weaker than that of indomethacin. Furthermore, it is seen that the ulcerogenic activities of the compounds Ia and Ib are much weaker than that of indomethacin.

TABLE 1

| Test compound | Dose (mg/kg) | Percent edema inhibition | | | | ED$_{40}$ value (mg/kg)* |
|---|---|---|---|---|---|---|
| | | 1 hour | 2 hours | 3 hours | 4 hours | |
| 10,11-dihydro-11-oxo-5H-dibenzo-[a,d]cycloheptene-2-acetic acid (Ia) | 25 | 28.2 | 41.8 | 44.5 | 41.0 | 13 |
| | 100 | 33.0 | 50.0 | 53.7 | 52.2 | |
| 8-fluoro-10,11-dihydro-11-oxo-5H-dibenzo[a,d]cycloheptene-2-acetic acid (Ib) | 25 | 32.4 | 45.3 | 43.4 | 41.9 | 15 |
| | 100 | 44.1 | 57.9 | 52.6 | 53.0 | |
| 10,11-dihydro-11-oxo-5H-dibenzo-[a,d]cycloheptene-3-acetic acid (Ic) | 25 | 32.8 | 29.4 | 25.5 | 24.0 | 94 |
| | 100 | 51.4 | 44.7 | 40.7 | 39.3 | |
| 10,11-dihydro-10-oxo-5H-dibenzo-[a,d]cycloheptene-2-acetic acid (Id) | 25 | 36.0 | 36.0 | 21.4 | 18.4 | — |
| | 100 | 44.6 | 39.0 | 28.1 | 21.4 | |
| 8-chloro-10,11-dihydro-10-oxo-5H-dibenzo[a,d]cycloheptene-2-acetic acid (Ie) | 25 | 4.5 | 8.6 | 3.0 | 2.3 | — |
| | 100 | −0.7 | 1.3 | −4.2 | −1.8 | |
| 10,11-dihydro-10-oxo-5H-dibenzo[a,d]cycloheptene-3-acetic acid (If) | 25 | −22.6 | −16.8 | −12.3 | −8.7 | — |
| | 100 | −23.5 | −21.4 | −9.1 | −5.5 | |
| 11-methoxy-5H-dibenzo[a,d]cyclo-heptene-2-acetic acid (Ig) | 100 | 25.5 | 40.6 | 42.6 | 37.1 | — |
| 2-(11-methoxy-5H-dibenzo[a,d]cyclo-hepten-2-yl)propionic acid (Ih) | 5 | 18.4 | 24.7 | 12.0 | 12.6 | 77 |
| | 20 | 28.1 | 22.9 | 26.8 | 26.8 | |
| | 50 | 35.6 | 32.9 | 35.4 | 35.7 | |
| 2-(10,11-dihydro-11-oxo-5H-dibenzo-[a,d]cyclohepten-2-yl)propionic acid (Ii) | 1 | 34.4 | 30.6 | 32.4 | 32.4 | 1.9 |
| | 5 | 35.8 | 54.0 | 51.7 | 50.9 | |
| | 10 | 50.0 | 55.0 | 54.6 | 54.6 | |
| Indomethacin (known compound) | 1 | 0 | 20.3 | 6.3 | 10.2 | 9.8 |
| | 5 | 3.9 | 31.1 | 25.9 | 31.7 | |
| | 10 | 37.2 | 45.3 | 41.8 | 40.5 | |

*A dose-response line was drawn from the inhibition percent obtained 3 hours after carrageenin injection, and the dose which caused 40% inhibition was measured.

TABLE 2

| Compound | Dose (mg/kg) | Number of writhing syndromes (Mean ± SE) | Inhibition (%) | ED$_{50}$ value (mg/kg)** |
|---|---|---|---|---|
| (Ii) | Control* | 22.9 ± 1.77 | 0 | 52.0 |
| | 10.0 | 19.7 ± 1.77 | 14.0 | |
| | 20.0 | 15.2 ± 1.28 | 33.6 | |
| | 40.0 | 12.5 ± 1.65 | 45.4 | |
| | 80.0 | 9.7 ± 1.93 | 57.6 | |
| Indomethacin | Control* | 20.0 + 1.31 | 0 | 5.0 |
| | 1.25 | 14.6 ± 2.35 | 27.7 | |
| | 2.5 | 12.0 ± 0.92 | 40.6 | |
| | 5.0 | 10.5 ± 1.40 | 48.0 | |
| | 10.0 | 7.6 ± 1.15 | 62.4 | |
| | 20.0 | 6.0 ± 0.94 | 70.3 | |

*A 1% carboxymethyl cellulose solution was orally administered in a dose of 10 ml/kg.
**A dose-response line was drawn from the percent inhibition of the administered groups, and the dose which caused 50% inhibition was calculated.

TABLE 3

| Compound | Dose (mg/kg) | Number of animals with ulcer/number of animals used (%) | Ulcer index* (Mean ± SE) | UD$_{50}$ value (mg/kg)** |
|---|---|---|---|---|
| Ii | 3.13 | 1/8 (12.5) | 0.13 ± 0.14 | 15.0 (7.6–29.7) |
| | 6.25 | 2/8 (25.0) | 0.25 ± 0.17 | |
| | 12.5 | 4/8 (50.0) | 0.50 ± 0.20 | |
| | 25.0 | 5/8 (62.5) | 0.88 ± 0.30 | |
| | 50.0 | 8/8 (100) | 2.75 ± 0.24 | |
| Indo-metha-cin | 3.13 | 0/8 (0) | 0 | 11.7 (7.8–17.6) |
| | 6.25 | 2/8 (25.0) | 0.37 ± 0.26 | |
| | 12.5 | 4/8 (50.0) | 1.38 ± 0.53 | |
| | 25.0 | 7/8 (87.5) | 1.88 ± 0.35 | |
| | 50.0 | 8/8 (100) | 3.12 ± 0.12 | |

*Calculated by the Adami's method.
**Calculated by the Litchfield-Wilcoxon's method. The parenthesized values show 95% confidence limits.

The following Examples illustrate the present invention more specifically.

EXAMPLE 1

(A) A solution of 3.8 g of 2-(4-carboxymethylbenzoyl)phenylacetic acid in 15 ml of methanol was added to 9.0 g of zinc amalgam, 17.5 ml of conc. hydrochloric acid and 7.5 ml of water. The mixture was heated under reflux for 5 hours with stirring. After the reaction, the reaction mixture was cooled, and the zinc amalgam was removed by decantation. Water (100 ml) was added, and the mixture was extracted with ether. The ethereal layer was washed with a saturated aqueous solution of sodium chloride. The ether was distilled off to afford a yellow oily product. Methanol (20 ml) was added to dissolve it. Then, 60 ml of a 10% sodium hydroxide solution was added to the solution, and the solution was heated under reflux for 3 hours with stirring. After the reaction, the reaction mixture was cooled, acidified with conc. hydrochloric acid, and extracted with ether. The ethereal layer was washed with a saturated aqueous solution of sodium chloride, and dried over anhydrous magnesium sulfate. The ether was then distilled off. The residue was chromatographed on a silica gel column using a mixture of chloroform and methanol (95:5) as an eluent. A solid was obtained from the eluate. Recrystallization from ether afforded 1.67 g of 2-(4-carboxymethylbenzyl)phenylacetic acid as colorless plate-like crystals having a melting point of 155° to 156° C.

NMR spectrum (CDCl$_3$/DMSO-d$_6$=10:1): δppm 3.53 (4H, s, —CH$_2$COOH×2), 3.97 (2H, s, —CH$_2$—), 6.9–7.3 (8H, aromatic proton), 10.25 (2H, bs, —COOH×2; disappeared in D$_2$O).

Compounds Nos. 1 to 7 shown in Table 4 were prepared in the same manner as above.

TABLE 4

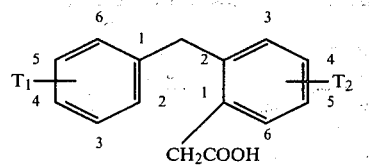

| Compound No. | $T_1$ | $T_2$ | Melting point (°C.) | Recrystallization solvent | Empirical formula | Calculated (%) C | Calculated (%) H | Found (%) C | Found (%) H |
|---|---|---|---|---|---|---|---|---|---|
| 1 | 4-CH$_2$COOH | H | 155-156 | Ethyl acetate | C$_{17}$H$_{16}$O$_4$ | 71.8 | 5.7 | 71.5 | 5.6 |
| 2 | 4-CH$_2$COOH | 5-F | 158-160 | Ethyl acetate/n-hexane | C$_{17}$H$_{15}$FO$_4$ | 67.5 | 5.0 | 67.8 | 5.0 |
| 3 | 4-CH$_2$COOH | 4-t-Bu | 138-139 | Ethyl acetate/n-hexane | C$_{21}$H$_{24}$O$_4$ | 74.1 | 7.1 | 73.8 | 7.3 |
| 4 | 3-CH$_2$COOH | H | 123.5-125 | Ethyl acetate/ether | C$_{17}$H$_{16}$O$_4$ | 71.8 | 5.7 | 71.7 | 5.6 |
| 5 | H | 5-CH$_2$COOH | 185-186 | Ethyl acetate | C$_{17}$H$_{16}$O$_4$ | 71.8 | 5.7 | 71.7 | 5.5 |
| 6 | 4-Cl | 5-CH$_2$COOH | 209-211 | Ethyl acetate/n-hexane | C$_{17}$H$_{15}$ClO$_4$ | 64.1 | 4.7 | 63.8 | 4.7 |
| 7 | H | 4-CH$_2$COOH | 201-203 | Ethyl acetate | C$_{17}$H$_{16}$O$_4$ | 71.8 | 5.7 | 71.7 | 5.7 |

(B) Polyphosphoric acid (20 g) was heated to 120° to 125° C., and with stirring, 2.9 g of 2-(4-carboxymethylbenzyl)phenylacetic acid was added. The mixture was stirred for 2 hours at the same temperature. After the reaction, the reaction mixture was cooled, and ice water was added. The solution was extracted with ethyl acetate. The ethyl acetate layer was washed with a saturated aqueous solution of sodium chloride, and dried over anhydrous magnesium sulfate. The ethyl acetate was then distilled off. The residue was chromatographed on a silica gel column using chloroform as an eluent. A slightly yellow solid was obtained from the eluate. Recrystallization from a mixture of ether and n-hexane afforded 1.52 g of 10,11-dihydro-11-oxo-5H-dibenzo[a,d]cycloheptene-2-acetic acid as colorless needle-like crystals having a melting point of 171° to 173°. The product is expressed by the following formula

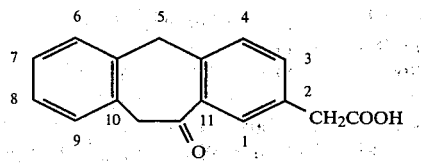

Elemental analysis value for C$_{17}$H$_{14}$O$_3$: Calculated (%): C 76.7 H 5.3; Found (%): C 76.3 H 5.2.

NMR spectrum (CDCl$_3$): δppm 3.65 (2H, s, —CH$_2$COOH), 4.12 (2H, s, —CH$_2$—), 4.18 (2H, s, —CH$_2$—), 7.0-7.4 (6H, aromatic proton), 7.94 (1H, s, proton at the 1-position), 10.26 (1H, bs, —COOH; disappeared in D$_2$O).

EXAMPLE 2

To a mixture of 15 g of polyphosphoric acid and 10 ml of sulfolane was added 1.5 g of 2-benzyl-5-carboxymethylphenylacetic acid, and the mixture was heated at 100° to 110° C. for 2 hours with stirring. After the reaction, the reaction mixture was cooled, and dissolved in ice water. The solution was extracted with ethyl acetate, and washed with water. The ethyl acetate layer was extracted with a 2% aqueous solution of sodium hydroxide. The aqueous layer was acidified with 10% hydrochloric acid. The precipitated solid was extracted with ethyl acetate, washed with a saturated aqueous solution of sodium chloride, and dried over magnesium sulfate. The ethyl acetate was then distilled off. Recrystallization of the residue from a mixture of ethyl acetate and n-hexane afforded 0.52 g of 10,11-dihydro-10-oxo-5H-dibenzo[a,d]cycloheptene-2-acetic acid as a colorless crystalline powder having a melting point of 163° to 165° C.

Elemental analysis values for C$_{17}$H$_{14}$O$_3$: Calculated (%): C 76.7 H 5.3; Found (%): C 76.7 H 5.4.

IR spectrum (KBr): An absorption attributed to the carboxyl group at 3500-2300 cm$^{-1}$ and 1700 cm$^{-1}$; and an absorption attributed to the carbonyl group at 1670 cm$^{-1}$.

EXAMPLE 3

(A) Thionyl chloride (6 ml) was added to 1.6 g of 2-(3-carboxymethylbenzyl)phenylacetic acid, and the mixture was heated under reflux for 3 hours with stirring. After the reaction, the reaction mixture was cooled, and the excess of thionyl chloride was distilled off. Thus, 2-(3-chlorocarbonylmethylbenzyl)phenylacetyl chloride as a slightly yellow oily substance was obtained quantitatively.

IR spectrum: An absorption attributed to the carboxylic acid chloride at 1795 cm$^{-1}$.

NMR spectrum (CDCl$_3$): δppm 3.96 (2H, s, —CH$_2$—), 4.01 (4H, s, —CH$_2$COCl×2), 6.8-7.4 (8H, aromatic proton).

(B) Dichloromethane (60 ml) was added to 1.8 g of 2-(3-chlorocarbonylmethylbenzyl)phenylacetyl chloride. To the resulting solution was added at a time 1.8 g of powdery anhydrous aluminum chloride with stirring and ice cooling. The mixture was stirred at this temperature for 45 minutes. After the reaction, the reaction mixture was poured into a mixture of ice water and hydrochloric acid, and the dichloromethane layer was separated. The aqueous layer was extracted with dichloromethane. The dichloromethane layers were combined, and washed with a saturated aqueous solution of sodium chloride. The dichloromethane was then distilled off. To the residue was added 30 ml of a 2% aqueous solution of sodium hydroxide, and the mixture was stirred at room temperature for 1 hour, and acidified with 10% hydrochloric acid. The separated oily material was extracted with ethyl acetate, washed with a saturated aqueous solution of sodium chloride, and dried over anhydrous magnesium sulfate. The ethyl acetate was distilled off. The residue was chromatographed on a silica gel column using chloroform as an eluent. Slightly yellow crystals were obtained from the eluate. Recrystallization from a mixture of ether and ethanol afforded 0.91 g of 10,11-dihydro-11-oxo-5H-dibenzo[a,d]cycloheptene-3-acetic acid as colorless needle-like crystals having a melting point of 178° to 181° C.

Elemental analysis values for $C_{17}H_{14}O_3$: Calculated (%): C 76.7 H 5.3; Found (%): C 76.9 H 5.3.

IR spectrum (KBr): An absorption attributed to the carboxyl group at 3500–2300 $cm^{-1}$ and 1695 $cm^{-1}$; and an absorption attributed to the carbonyl group at 1660 $cm^{-1}$.

NMR spectrum ($CDCl_3/DMSO-d_6=5:1$) δppm 3.59 (2H, s, —CH₂COOH), 4.12 (2H, s, —CH₂—), 4.25 (2H, s, —CH₂—), 6.9–8.0 (7H, aromatic proton).

In the same manner as above, the following compounds were produced.

(i)
8-Chloro-10,11-dihydro-10-oxo-5H-dibenzo[a,d]cycloheptene-2-acetic acid

Form: slightly yellow needle-like crystals.
Melting point: 167° to 169° C. (recrystallized from ethyl acetate/n-hexane).
Elemental analysis values for $C_{17}H_{13}ClO_3$: Calculated (%): C 67.9 H 4.4; Found (%): C 67.6 H 4.7.

(ii)
8-Fluoro-10,11-dihydro-11-oxo-5H-dibenzo[a,d]cycloheptene-2-acetic acid

Form: colorless needle-like crystals.
Melting point: 172° to 174° C. (recrystallized from ethyl acetate/n-hexane).
Elemental analysis values for $C_{17}H_{13}FO_3$: Calculated (%): C 71.8 H 4.6; Found (%): C 72.0 H 4.4.

EXAMPLE 4

(A) Dry benzene (15 ml) and 10 ml of thionyl chloride were added to 3.0 g of 2-[4-(1-carboxyethyl)benzyl]phenylacetic acid, and the mixture was heated under reflux for 2 hours with stirring. After the reaction, the reaction mixture was cooled, and benzene and the excess of thionyl chloride were distilled off. There was quantitatively obtained 2-[4-(1-chlorocarbonylethyl)benzyl]phenylacetyl chloride as a slightly yellow oily substance.

IR spectrum (neat): An absorption attributed to the carboxylic acid chloride group at 1790 $cm^{-1}$.

(B) In 100 ml of 1,2-dichloroethane was dissolved 3.36 g of 2-[4-(1-chlorocarbonylethyl)benzyl]phenylacetyl chloride. The solution was cooled to −30° C., and 6.0 g of powdery anhydrous aluminum chloride was added at a time. The mixture was stirred at this temperature for 30 minutes. After the reaction, the reaction mixture was poured into ice water, and the 1,2-dichloroethane layer was separated and washed with a saturated aqueous solution of sodium chloride. The 1,2-dichloroethane was distilled off. The residue was dissolved in 10 ml of ether, and the solution was extracted with 50 ml of a 5% aqueous solution of sodium hydroxide. The aqueous layer was acidified with 10% hydrochloric acid under ice cooling. The separated oily substance was extracted with ether, washed with a saturated aqueous solution of sodium chloride, and dried over anhydrous magnesium sulfate. The ether was then distilled off. Recrystallization of the residue from ether afforded 1.23 g of 2-(10,11-dihydro-11-oxo-5H-dibenzo[a,d]cyclohepten-2-yl)propionic acid as colorless prismatic crystals having a melting point of 134° to 136° C.

Elemental analysis values for $C_{18}H_{16}O_3$: Calculated (%): C 77.1 H 5.8; Found (%): C 76.8 H 5.7.

IR spectrum (KBr): An absorption attributed to the carboxyl group at 3500–2300 $cm^{-1}$ and 1685 $cm^{-1}$; and an absorption attributed to the carbonyl group at 1665 $cm^{-1}$.

NMR spectrum ($CDCl_3$):

| δ ppm | |
|---|---|
| 1.44 (3H, d, —CH—CH₃), <br>                 \| <br>               COOH | |
| 3.70 (1H, q, —CHCH₃), <br>              \| <br>             COOH | |
| 4.13 (2H, s, —CH₂—), <br> 4.20 (2H, s, —CH₂—), <br> 7.0–7.5 (6H, aromatic proton), <br> 8.00 (1H, s, proton at the 1-position), <br> 9.95 (1H, br, —COOH; disappeared in D₂O). | |

EXAMPLE 5

In 100 ml of dichloromethane was dissolved 3.36 g of 2-[4-(1-chlorocarbonylethyl)benzyl]phenylacetyl chloride. The solution was cooled to −30° C., and 6 ml of antimony pentachloride was added at a time. The mixture was stirred at this temperature for 30 minutes. After the reaction, the reaction mixture was poured into ice water. The dichloromethane layer was separated, and washed with a saturated aqueous solution of sodium chloride. The dichloromethane was distilled off, and the residue was dissolved in 10 ml of ether. The solution was extracted with 50 ml of a 5% aqueous solution of sodium hydroxide. The aqueous layer was acidified with 10% hydrochloric acid under ice cooling. The separated oily substance was extracted with ether, washed with a saturated aqueous solution of sodium chloride, and dried over anhydrous magnesium sulfate. The ether was then distilled off. Recrystallization of the residue from ether afforded 1.97 g of 2-(10,11-dihydro-11-oxo-5H-dibenzo[a,d]cyclohepten-2-yl)propionic acid as colorless prismatic crystals having a melting point of 134° to 136° C.

EXAMPLE 6

(A) Dry benzene (10 ml) and 0.7 ml of thionyl chloride were added to 0.295 g of 2-(4-carboxymethylbenzyl)phenylacetic acid, and the mixture was heated under reflux for 4 hours with stirring. After the reaction, the reaction mixture was cooled, and the solvent was distilled off to afford quantitatively 2-(4-chlorocarbonylmethylbenzyl)phenylacetyl chloride as a brown oily substance.

IR spectrum: An absorption attributed to the carboxylic acid chloride group at 1780 $cm^{-1}$.

(B) In 10 ml of dichloroethane was dissolved 0.33 g of 2-(4-chlorocarbonylmethylbenzyl)phenylacetyl chloride, and 0.58 g of anhydrous stannic chloride was added to the solution under ice cooling and stirring. The mixture was stirred under ice cooling for 30 minutes, and then at room temperature for 1 hour. After the reaction, the reaction mixture was poured into ice water. The dichloroethane layer was separated, and the aqueous layer was extracted with chloroform. The dichloroethane layer and the chloroform layer were combined, and washed with a saturated aqueous solution of sodium chloride. Then, a 10% aqueous solution of sodium hydroxide was added, and the mixture was vigorously stirred at room temperature for 30 minutes. The aqueous layer was separated and acidified with 10% hydrochloric acid. The separated oily substance was extracted with ether. The ethereal layer was washed with a saturated aqueous solution of sodium chloride, and dried over anhydrous sodium sulfate. The ether was distilled off. Recrystallization of the residue from a mixture of ether and n-hexane afforded 0.132 g of 10,11-dihydro-11-oxo-5H-dibenzo[a,d]cycloheptene-2-acetic acid as colorless needle-like crystals having a melting point of 171° to 173° C.

EXAMPLE 7

In 50 ml of dichloroethane was dissolved in 3.0 g of 2-benzyl-4-chlorocarbonylmethylphenylacetyl chloride. With stirring at room temperature, 5.0 g of a solution of boron trifluoride etherate was added to the solution. The mixture was stirred for 2 hours, and worked up in the same way as in Example 6 to afford 1.42 g of 10,11-dihydro-10-oxo-5H-dibenzo[a,d]cycloheptene-3-acetic acid as a colorless crystalline powder (recrystallized from a mixture of methanol and n-hexane) having a melting point of 186° to 188° C.

Elemental analysis values for $C_{17}H_{14}O_3$: Calculated (%): C 76.7 H 5.3; Found (%): C 76.5 H 5.1.

EXAMPLE 8

(A) A mixture of 25 ml of 30% aqueous ammonia and 12.5 ml of water was added to 17.5 g of active zinc powder. The mixture was heated at 80° C. with stirring. A saturated aqueous solution of copper sulfate (0.8 ml) was added, and then, a solution of 3.0 g of 4-t-butyl-2-(4-carboxymethylbenzoyl)phenylacetic acid in 25 ml of ethanol was added dropwise. The mixture was stirred at the same temperature for 30 hours. After the reaction, the reaction mixture was cooled, and the insoluble matter was separated by filtration. The filtrate was acidified with conc. hydrochloric acid, and extracted with ethyl acetate. The extract was washed with water and then with a saturated aqueous solution of sodium chloride, and dried over anhydrous magnesium sulfate. The ethyl acetate was distilled off. Recrystallization of the residue from a mixture of ethyl acetate and n-hexane afforded 1.7 g of 4-t-butyl-2-(4-carboxymethylbenzyl)phenylacetic acid as colorless needle-like crystals having a melting point of 138° to 139° C.

NMR spectrum (CDCl$_3$): δppm 1.24 [9H, s, C(CH$_3$)$_3$], 3.58 (4H, bs, —CH$_2$COOH×2), 3.97 (2H, s, —CH$_2$—), 6.9–7.3 (7H, aromatic proton), 10.51 (2H, bs, —COOH×2; disappeared in D$_2$O).

(B) The resulting carboxylic acid was converted to 4-t-butyl-2-(4-chlorocarbonylmethylbenzyl)phenylacetyl chloride in a customary manner. Then, 1.4 g of the resulting acid chloride was dissolved in 21 ml of carbon disulfide, and with stirring at room temperature, 1.1 g of zinc chloride was added. The mixture was stirred for 2 hours under reflux. After the reaction, the reaction mixture was cooled, and poured into ice water. The carbon disulfide layer was separated. The aqueous layer was extracted with chloroform. The carbon disulfide layer and the chloroform layer were combined, washed with a saturated aqueous solution of sodium chloride, and extracted with a 10% aqueous solution of sodium hydroxide. The aqueous layer was acidified with 10% hydrochloric acid, and the separated oily substance was extracted with ethyl acetate. The ethyl acetate layer was dried over anhydrous sodium sulfate. The ethyl acetate was distilled off, and the residue was chromatographed on a silica gel column using chloroform as an eluent. From the eluate, 0.48 g of 7-t-butyl-10,11-dihydro-11-oxo-5H-dibenzo[a,d]-cycloheptene-2-acetic acid was obtained as an amorphous solid.

IR spectrum (KBr): An absorption attributed to the carboxyl group at 3600–2400 cm$^{-1}$ and 1700 cm$^{-1}$; and an absorption attributed to the carbonyl group at 1670 cm$^{-1}$.

NMR spectrum (CDCl$_3$): δppm: 1.30 (9H, s, —CH$_3$×3), 3.60 (2H, s, —CH$_2$—), 4.12 (2H, s, —CH$_2$—), 4.19 (2H, s, —CH$_2$—), 7.0–8.2 (6H, aromatic proton), 8.65 (1H, bs, —COOH; disappeared in D$_2$O).

EXAMPLE 9

In 3 ml of a 12% ethanol solution of hydrogen chloride was dissolved 0.14 g of 10,11-dihydro-11-oxo-5H-dibenzo[a,d]cycloheptene-3-acetic acid obtained in Example 3. The solution was heated under reflux for 30 minutes with stirring. After the reaction, the reaction mixture was cooled, and the solvent was distilled off. Water was added to the residue, and the mixture was extracted with ether. The ethereal layer was washed with a saturated aqueous solution of sodium chloride, and dried over anhydrous magnesium sulfate. Then, the ether was distilled off. The residue was chromatographed on a silica gel column using benzene as an eluent. From the eluate, 0.12 g of ethyl 10,11-dihydro-11-oxo-5H-dibenzo[a,d]cycloheptene-3-acetate was obtained as a slightly yellow oily substance.

Refractive index: $[n_D^{24}] = 1.5845$.

Elemental analysis values for $C_{19}H_{18}O_3$: Calculated (%): C 77.5 H 6.2; Found (%): C 77.3 H 6.4.

NMR spectrum (CDCl$_3$): δppm 1.20 (3H, t, —OCH$_2$CH$_3$), 3.47 (2H, s, —CH$_2$COOC$_2$H$_5$), 4.06 (2H, s, —CH$_2$—), 4.10 (2H, q, —OCH$_2$CH$_3$), 4.15 (2H, s, —CH$_2$—), 7.0–8.1 (7H, aromatic proton).

EXAMPLE 10

In 50 ml of a saturated methanol solution of hydrogen chloride was dissolved 6.12 g of 10,11-dihydro-11-oxo-5H-dibenzo[a,d]cycloheptene-2-acetic acid obtained in Example 1. The solution was stirred for 2 hours under ice cooling. After the reaction, the reaction mixture was worked up in the same way as in Example 9 to afford 6.4 g of methyl 10,11-dihydro-11-oxo-5H-dibenzo[a,d]cycloheptene-2-acetate as colorless needle-like crystals (recrystallized from ether/n-hexane) having a melting point of 111° to 112.5° C.

Elemental analysis values for $C_{18}H_{16}O_3$: Calculated (%): C 77.1 H 5.6; Found (%): C 77.2 H 5.7.

EXAMPLE 11

In 50 ml of dry methanol was dissolved 6.3 g of methyl 10,11-dihydro-11-oxo-5H-dibenzo[a,d]cycloheptene-2-acetate obtained in Example 10. Thionyl chloride (7 g) was added, and the solution was heated under reflux for 2 hours with stirring. After the reaction, the reaction mixture was cooled, and methanol was distilled off. The residue was dissolved in 200 ml of benzene. The benzene solution was washed with a saturated aqueous solution of sodium chloride, and dried over anhydrous magnesium sulfate. The benzene was then distilled off. The residue was chromatographed on a silica gel column using benzene as an eluate. A slightly yellow solid was obtained from the eluate. Recrystallization from n-hexane afforded 4.6 g of methyl 11-methoxy-5H-dibenzo[a,d]cycloheptene-2-acetate as colorless needle-like crystals having a melting point of 72° to 73° C.

IR spectrum (KBr): An absorption attributed to the ester group at 1730 cm$^{-1}$; and an absorption attributed to the enol ether group at 1240 cm$^{-1}$.

NMR spectrum (CDCl$_3$): δppm 3.45 (2H, s, —CH$_2$—), 3.61 (3H, s, —COOCH$_3$), 3.65 (2H, s, —CH$_2$—), 3.87 (3H, s, —OCH$_3$), 6.25 (1H, s, proton at the 10-position), 7.0–7.7 (7H, aromatic proton).

EXAMPLE 12

In 18 ml of methanol was dissolved 2.1 g of 10,11-dihydro-11-oxo-5H-dibenzo[a,d]cycloheptene-2-acetic acid obtained in Example 1. Thionyl chloride (2.1 g) was added, and the solution was heated under reflux for 3 hours with stirring. After the reaction, the reaction mixture was cooled, and then worked up in the same way as in Example 11 to afford 2.5 g of methyl 11-methoxy-5H-dibenzo[a,d]cycloheptene-2-acetate as colorless needle-like crystals having a melting point of 72° to 73° C.

Elemental analysis values for C$_{19}$H$_{18}$O$_3$: Calculated (%): C 77.5 H 6.2; Found (%): C 77.6 H 6.3.

EXAMPLE 13

In 2 ml of ethanol was dissolved 0.1 g of 10,11-dihydro-10-oxo-5H-dibenzo[a,d]cycloheptene-3-acetic acid obtained in Example 7. Thionyl chloride (0.1 g) was added, and the solution was heated under reflux for 2 hours with stirring. After the reaction, the reaction mixture was cooled, and then worked up in the same way as in Example 11 to afford 0.08 g of ethyl 10-ethoxy-5H-dibenzo[a,d]cycloheptene-3-acetate as a colorless oily substance.

Refractive index: n$_D^{24}$=1.5944.

Elemental analysis values for C$_{21}$H$_{22}$O$_3$: Calculated (%): C 78.2 H 6.9; Found (%): C 77.9 H 6.7.

IR spectrum (neat): An absorption attributed to the ester group at 1720 cm$^{-1}$; and an absorption attributed to the enol ether group at 1235 cm$^{-1}$.

EXAMPLE 14

Under a nitrogen stream, 1.2 ml of diisopropylamine was dissolved in 10 ml of dry tetrahydrofuran. 5 ml of a 15% n-hexane solution of n-butyl lithium was added with stirring to the solution cooled with acetone-dry ice. The mixture was stirred for 20 minutes under cooling with acetone-dry ice. Then, a solution of 1.77 g of methyl 11-methoxy-5H-dibenzo[a,d]cycloheptene-2-acetate obtained in Example 12 in 6 ml of dry tetrahydrofuran was added gradually. The mixture was stirred for 20 minutes. A solution of 0.4 g of methyl iodide in 3 ml of dry tetrahydrofuran was gradually added, and the mixture was stirred for 1 hour. To the resulting reaction mixture was added 5 ml of a saturated aqueous solution of ammonium chloride. The tetrahydrofuran layer was separated, and dried over anhydrous magnesium sulfate. The solvent was distilled off. The resulting slightly yellow oily substance was chromatographed on a silica gel column using benzene as an eluent. From the eluate, 1.75 g of methyl 2-(11-methoxy-5H-dibenzo[a,d]cyclohepten-2-yl)propionate as a colorless oily substance.

Refractive index: n$_D^{24}$=1.6058.

NMR spectrum (CDCl$_3$):

| δ ppm | |
|---|---|
| | 1.44 (3H, d, —CH—CH$_3$), <br>              | <br>          COOCH$_3$ |
| | 3.54 (3H, s, —COOCH$_3$), |
| | 3.56 (1H, q, —CH—CH$_3$), <br>            | <br>          COOCH$_3$ |
| | 3.60 (2H, s, —CH$_2$—), <br> 3.85 (3H, s, —OCH$_3$), <br> 6.23 (1H, s, proton at the 10-position), <br> 7.0–7.5 (7H, aromatic proton). |

EXAMPLE 15

Small pieces of ferric nitrate nonahydrate were added to 75 ml of liquid ammonia, and subsequently 0.733 g of metallic sodium was added little by little. The mixture was stirred for 30 minutes. To the stirred mixture was added dropwise over the course of 10 minutes a solution of 6.25 g of methyl 11-methoxy-5H-dibenzo[a,d]cyclohepten-2-acetate obtained in Example 12 in 12 ml of dry toluene. The mixture was stirred for 25 minutes, and a solution of 1.98 ml of methyl iodide in 2 ml of dry toluene was added dropwise over the course of 2 minutes. The mixture was further stirred for 1 hour, and then 1.83 g of ammonium chloride and 12 ml of toluene were added. Ammonia was released at room temperature. Then, 24 ml of 10% hydrochloric acid was added under ice cooling and stirring, and the mixture was stirred for 15 minutes. Ether (100 ml) and 100 ml of water were added to extract the solution. The organic layer was successively washed with water, a 10% aqueous solution of sodium thiosulfate and a saturated aqueous solution of sodium chloride, and dried over anhydrous magnesium sulfate. The solvent was distilled off. The residue was chromatographed on a silica gel column using benzene as an eluent. From the eluate, 5.91 g of methyl 2-(11-methoxy-5H-dibenzo[a,d]cyclohepten-2-yl)propionate was obtained as a colorless oily substance.

EXAMPLE 16

Six milliliters of 47% hydrobromic acid was added to 0.51 g of methyl 11-methoxy-5H-dibenzo[a,d]cycloheptene-2-acetate obtained in Example 12, and the mixture was stirred at room temperature for 2 hours. After the reaction, water was added to the reaction mixture, and the mixture was extracted with ether. The ethereal layer was washed with a saturated aqueous solution of sodium chloride, and the ether was distilled off. Recrystallization of the residue from n-hexane afforded 0.43 g of methyl 10,11-dihydro-11-oxo-5H-dibenzo[a,d]cycloheptene-2-acetate as colorless needle-like crystals having a melting point of 111° to 112° C.

EXAMPLE 17

In 10 ml of benzene was dissolved 1.46 g of methyl 2-(11-methoxy-5H-dibenzo[a,d]cyclohepten-2-yl)propionate obtained in Example 14, and 16 ml of 47% hydrobromic acid was added. The mixture was vigorously stirred at room temperature for 4 hours. After the reaction, water (50 ml) was added to the reaction mixture. The benzene layer was separated, washed with a saturated aqueous solution of sodium chloride, and dried over anhydrous sodium sulfate. The benzene was distilled off. Recrystallization of the residue from a mixture of ether and n-hexane afforded 1.21 g of methyl 2-(10,11-dihydro-11-oxy-5H-dibenzo[a,d]cyclohepten-2-yl)propionate as colorless needle-like crystals having a melting point of 121° to 123° C.

Elemental analysis values for $C_{19}H_{18}O_3$: Calculated (%): C 77.5 H 6.2; Found (%): C 77.1 H 5.9.

EXAMPLE 18

In 2 ml of methanol was dissolved 0.1 g of methyl 10,11-dihydro-11-oxo-5H-dibenzo[a,d]cycloheptene-2-acetate obtained in Example 16, and 6 ml of a 10% aqueous solution of sodium hydroxide was added. The mixture was heated under reflux for 2 hours with stirring. After the reaction, the reaction mixture was cooled, and water was added. The mixture was acidified with 10% hydrochloric acid, and the precipitated solid was extracted with ether. The ethereal layer was washed with a saturated aqueous solution of sodium chloride and then dried over anhydrous magnesium sulfate. The ether was distilled off. Recrystallization of the residue from a mixture of ether and n-hexane afforded 0.082 g of 10,11-dihydro-11-oxo-5H-dibenzo[a,d]cycloheptene-2-acetic acid as colorless needle-like crystals having a melting point of 171° to 173° C.

In the same manner as above, the following compounds were produced.

(i)
2-(10,11-dihydro-11-oxo-5H-dibenzo[a,d]cyclohepten-2-yl)propionic acid

Form: colorless needle-like crystals (recrystallized from n-hexane).
Melting point: 135° to 136° C.

(ii) 11-methoxy-5H-dibenzo[a,d]cycloheptene-2-acetic acid

Form: colorless needle-like crystals (recrystallized from ethyl acetate/n-hexane).
Melting point: 174° to 175° C.
Elemental analysis values for $C_{18}H_{16}O_3$: Calculated (%): C 77.1 H 5.8; Found (%): C 76.8 H 5.5.

(iii)
2-(11-methoxy-5H-dibenzo[a,d]cyclohepten-2-yl)propionic acid

Form: colorless amorphous solid.
IR spectrum (KBr):
An absorption attributed to the carboxyl group at 3500–2300 cm$^{-1}$ and 1695 cm$^{-1}$; and an absorption attributed to the enol ether group at 1240 cm$^{-1}$.
NMR spectrum (CDCl$_3$):

| δ ppm | |
|---|---|
| 1.42 (3H, d, —CHCH$_3$),<br>\|<br>COOH | |
| 3.65 (1H, q, —CHCH$_3$),<br>\|<br>COOH | |
| 3.85 (3H, s, —OCH$_3$), | |
| 6.23 (1H, s, proton at the 10-position), | |
| 6.95–7.70 (7H, aromatic proton), | |
| 9.5 (1H, br, —COOH; disappeared in D$_2$O). | |

EXAMPLE 19

Six milliliters of 47% hydrobromic acid was added to 0.32 g of methyl 11-methoxy-5H-dibenzo[a,d]cycloheptene-2-acetate obtained in Example 11, and the mixture was stirred at 100° to 125° C. for 30 minutes. After the reaction, the reaction mixture was cooled, and water was added. The mixture was extracted with ether. The ethereal layer was washed with a saturated aqueous solution of sodium chloride, and dried over anhydrous magnesium sulfate. The ether was distilled off. Recrystallization of the residue from a mixture of methanol and n-hexane afforded 0.22 g of 10,11-dihydro-11-oxo-5H-dibenzo[a,d]cycloheptene-2-acetic acid as colorless needle-like crystals.

EXAMPLE 20

In 1 ml of xylene was dissolved 0.1 g of ethyl 10-ethoxy-5H-dibenzo[a,d]cycloheptene-3-acetate obtained in Example 13, and 5 ml of 47% hydrobromic acid was added. The mixture was heated under reflux for 2 hours with vigorous stirring. After the reaction, the reaction mixture was cooled, and then worked up in the same way as in Example 19 to afford 0.07 g of 10,11-dihydro-10-oxo-5H-dibenzo[a,d]cycloheptene-3-acetic acid as a colorless crystalline powder (recrystallized from a mixture of methanol and n-hexane) having a melting point of 186° to 187.5° C.

REFERENTIAL EXAMPLE 1

(A) Anhydrous aluminum chloride (456 g) was suspended in 1.1 liters of 1,2-dichloroethane, and a solution of 328.6 g of acetyl chloride in 2 liters of 1,2-dichloroethane was added dropwise under ice cooling and stirring. The mixture was stirred for 30 minutes under ice cooling, and then, a solution of 456 g of ethyl 2-benzylbenzoate in 0.6 liter of 1,2-dichloroethane was added dropwise. The mixture was stirred for 2.5 hours at room temperature. After the reaction, the reaction mixture was poured into 4 liters of a mixture of ice water and conc. hydrochloric acid, and the 1,2-dichloroethane layer was separated. The aqueous layer was extracted with 1,2-dichloroethane. The 1,2-dichloroethane layers were combined, washed with a 5% aqueous solution of sodium hydroxide and a saturated aqueous solution of sodium chloride, and dried over anhydrous magnesium sulfate. The solvent was distilled off. The resulting yellow oily substance was distilled under reduced pressure to afford 510 g of 4-(2-ethoxycarbonylbenzyl)acetophenone as a pale yellow oily substance having a boiling point of 164° to 165° C. (0.15 to 0.17 mmHg).

Elemental analysis values for $C_{18}H_{18}O_3$: Calculated (%): C 76.6 H 6.4; Found (%): C 76.5 H 6.3.

IR spectrum (neat): An absorption attributed to the ester group at 1715 cm$^{-1}$; and an absorption attributed to the carbonyl group at 1680 cm$^{-1}$.

NMR spectrum (CDCl$_3$): δppm 1.30 (3H, t, J=7.5 Hz, —COOCH$_2$CH$_3$), 2.49 (3H, s, —COCH$_3$), 4.24 (2H, q, J=7.5 Hz, —COOCH$_2$CH$_3$), 4.40 (2H, s, —CH$_2$—), 7.0–8.1 (8H, aromatic proton).

(B) A solution of 130 g of 4-(2-ethoxycarbonylbenzyl)acetophenone in 0.2 liter of diglyme was added dropwise to a solution of 34.1 g of sodium borohydride in 0.6 liter of diglyme. Then, a solution of 45.5 g of aluminum chloride in 0.17 liter of diglyme was added dropwise, and the mixture was stirred at room temperature for 1 hour and then at 50° C. for 1 hour. Under ice cooling, 5 liters of a mixture of ice and 10% hydrochloric acid was added, and the mixture was vigorously stirred. The insoluble matter was collected by filtration, dried, and recrystallized from benzene to afford 136 g of (1-hydroxyethyl)-4-(2-hydroxymethylbenzyl)benzene as colorless needle-like crystals having a melting point of 96° to 97° C.

Elemental analysis values for $C_{16}H_{18}O_2$: Calculated (%): C 79.3 H 7.5; Found (%): C 79.3 H 7.5.

IR spectrum (KBr): An absorption attributed to the hydroxyl group at 3320 cm$^{-1}$.

NMR spectrum (CDCl$_3$/DMSO-d$_6$=10:1):

| δ ppm | 1.38 (3H, d, J = 7.5 Hz, OH |
| --- | --- |
| | $\quad\quad\quad\quad\quad\quad\quad\quad$ \| |
| | $\quad\quad\quad\quad\quad\quad$ —CH—CH$_3$), |
| | 3.94 (2H, s, —CH$_2$—), |
| | 4.49 (2H, s, —CH$_2$OH), |
| | 4.50 (2H, s, —OH × 2; disappeared in D$_2$O), |
| | 4.77 (1H, q, J = 7.5 Hz, OH |
| | $\quad\quad\quad\quad\quad\quad\quad\quad\quad$ \| |
| | $\quad\quad\quad\quad\quad\quad$ —CH—CH$_3$), |
| | 6.9-7.6 (8H, aromatic proton). |

(C) In 20 ml of benzene was suspended 4.85 g of (1-hydroxyethyl)-4-(2-hydroxymethylbenzyl)benzene, and with stirring under ice cooling, 6.0 ml of thionyl chloride was added dropwise. The mixture was stirred at room temperature for 2 hours and then at 65° C. for 15 minutes. After the reaction, the reaction mixture was cooled, and the solvent was distilled off. The residue was dissolved in ether, and the ethereal layer was washed with a 10% aqueous solution of sodium bicarbonate and a saturated aqueous solution of sodium chloride and dried over anhydrous magnesium sulfate. The ether was distilled off to afford 5.6 g of (1-chloroethyl)-4-(2-chloromethylbenzyl)benzene as a colorless liquid.

Elemental analysis values for $C_{16}H_{16}Cl_2$: Calculated (%): C 68.8 H 5.8; Found (%): C 68.9 H 5.8.

NMR spectrum (CDCl$_3$):

| ppm | 1.81 (3H, d, J = 7.5 Hz, Cl |
| --- | --- |
| | $\quad\quad\quad\quad\quad\quad\quad\quad$ \| |
| | $\quad\quad\quad\quad\quad\quad$ —CH—CH$_3$), |
| | 4.11 (2H, s, —CH$_2$—), |
| | 4.49 (2H, s, —CH$_2$Cl), |
| | 5.03 (1H, q, J = 7.5 Hz, Cl |
| | $\quad\quad\quad\quad\quad\quad\quad\quad\quad$ \| |
| | $\quad\quad\quad\quad\quad\quad$ —CH—CH$_3$), |
| | 6.95-7.45 (8H, aromatic proton). |

(D) Sodium cyanide (2.4 g) and 0.8 g of benzyl triethyl ammonium chloride were added to 30 ml of dimethyl formamide, and with stirring, a solution of 5.6 g of (1-chloroethyl)-4-(2-chloromethylbenzyl)benzene in 10 ml of dimethyl formamide was added. The mixture was stirred at 40° C. for 1 hour and then at 70° C. for 20 hours. After the reaction, the reaction mixture was cooled, and 70 ml of water was added. The mixture was extracted with ether. The ethereal layer was washed with water, dried over anhydrous magnesium sulfate and distilled off to remove the ether. The resulting pale yellow oily substance was chromatographed on a silica gel column using benzene as an eluent. From the eluate, 3.4 g of (1-cyanoethyl)-4-(2-cyanomethylbenzyl)benzene was obtained as a colorless liquid. This compound crystallized by stimulating the reactor wall through addition of n-hexane. Recrystallization from a mixture of ether and n-hexane afforded colorless needle-like crystals having a melting point of 61° to 64° C.

Elemental analysis values for $C_{18}H_{16}N_2$: Calculated (%): C 83.0 H 6.2 N 10.8; Found (%): C 82.6 H 6.2 N 10.4.

IR spectrum (KBr): An absorption attributed to the cyano group at 2240 cm$^{-1}$.

NMR spectrum (CDCl$_3$):

| δ ppm | 1.37 (3H, d, J = 7.5 Hz, CN |
| --- | --- |
| | $\quad\quad\quad\quad\quad\quad\quad\quad\quad$ \| |
| | $\quad\quad\quad\quad\quad\quad$ —CHCH$_3$), |
| | 3.52 (2H, s, —CH$_2$CN), |
| | 3.83 (1H, q, J = 7.5 Hz, CN |
| | $\quad\quad\quad\quad\quad\quad\quad\quad\quad$ \| |
| | $\quad\quad\quad\quad\quad\quad$ —CHCH$_3$), |
| | 4.00 (2H, s, —CH$_2$—), |
| | 6.95-7.5 (8H, aromatic proton). |

(E) In 5 ml of ethanol was dissolved 1.72 g of (1-cyanoethyl)-4-(cyanomethylbenzyl)benzene, and 3 ml of a 50% aqueous solution of potassium hydroxide was added. The mixture was heated under reflux for 15 hours. After the reaction, the reaction mixture was cooled, and 30 ml of water was added. The mixture was washed with ether, and the aqueous layer was acidified with conc. hydrochloric acid. The precipitated solid was extracted with ethyl acetate. The ethyl acetate layer was washed with a saturated aqueous solution of sodium chloride, dried over anhydrous magnesium sulfate, and distilled off to remove the ethyl acetate. The residual brown solid was recrystallized from benzene to afford 1.41 g of 2-[4-(1-carboxyethyl)benzyl]phenylacetic acid as colorless prismatic crystals having a melting point of 135° to 137° C.

Elemental analysis values for $C_{18}H_{18}O_4$: Calculated (%): C 72.5 H 6.1; Found (%): C 72.2 H 6.1.

IR spectrum (KBr): An absorption attributed to the carboxyl group at 3600-2300 cm$^{-1}$ and 1695 cm$^{-1}$.

NMR spectrum (CDCl$_3$/DMSO-d$_6$=10:1):

| δ ppm | 1.38 (3H, d, J = 7.5 Hz, COOH |
| --- | --- |
| | $\quad\quad\quad\quad\quad\quad\quad\quad\quad\quad$ \| |
| | $\quad\quad\quad\quad\quad\quad$ —CH—CH$_3$), |
| | 3.52 (2H, s, —CH$_2$COOH), |
| | 3.60 (1H, q, J = 7.5 Hz, COOH |
| | $\quad\quad\quad\quad\quad\quad\quad\quad\quad\quad\quad$ \| |
| | $\quad\quad\quad\quad\quad\quad$ —CH—CH$_3$), |
| | 3.95 (2H, s, —CH$_2$—), |
| | 7.12 (8H, aromatic proton), |
| | 10.8-12.2 (2H, br, —COOH × 2; disappeared in D$_2$O). |

REFERENTIAL EXAMPLE 2

(A) Ethyl 2-benzylbenzoate (54.0 g) was dissolved in 100 ml of dichloromethane, and with stirring, 121.3 g of stannic chloride was added while cooling the solution with a mixture of ice and sodium chloride. The mixture was stirred for 1 hour. Subsequently, 86 g of α,α-dichloromethyl methyl ether was added dropwise over 1 hour, and then the mixture was stirred at room temperature for 3 hours. After the reaction, the reaction mixture was poured into 1 liter of ice water, and stirred. The dichloromethane layer was separated, washed with water, a saturated aqueous solution of sodium carbonate and subsequently with a saturated aqueous solution of sodium chloride, and dried over anhydrous magnesium sulfate. The dichloromethane was distilled off. To the residue was added 250 ml of a saturated aqueous solution of sodium bisulfite, and the mixture was vigorously stirred. The precipitated crystals were collected by filtration, and washed with 100 ml of a saturated aqueous solution of sodium chloride and then with 100 ml of ether. The crystals were then suspended in 500 ml of water, and with stirring, 120 g of sodium carbonate was added little by little over the course of 15 minutes. The mixture was stirred for 2 hours. The separated oily substance was extracted with 300 ml of ether. The ethereal layer was washed with water and dried over anhydrous magnesium sulfate. The ether was distilled off to afford 43.3 g of 4-(2-ethoxycarbonylbenzyl)benzaldehyde as a red oily substance.

IR spectrum (neat): An absorption attributed to the carbonyl group at 1705 cm$^{-1}$.

NMR spectrum (CDCl$_3$): δppm 1.25 (3H, t, —CO$_2$CH$_2$CH$_3$), 4.20 (2H, q, —CO$_2$CH$_2$CH$_3$), 4.41 (2H, s, —CH$_2$—), 7.0–8.0 (8H, aromatic proton), 9.86 (1H, s, —CHO).

(B) Sodium borohydride (7.6 g) was added to 200 ml of diglyme, and with stirring at room temperature, a solution of 39.3 g of 4-(2-ethoxycarbonylbenzyl)benzaldehyde in 50 ml of diglyme was added dropwise over the course of 25 minutes. Subsequently, a solution of 9.33 g of anhydrous aluminum chloride in 50 ml of diglyme was added dropwise over the course of 15 minutes. The mixture was stirred at room temperature for 2 hours, and then at 45° to 50° C. for 1 hour. The reaction mixture was poured into about 3 liters of ice water, and stirred. The precipitated crystals were collected by filtration, washed with water, dried, and recrystallized from benzene to afford 28.2 g of 4-(2-hydroxymethylbenzyl)benzyl alcohol as colorless needle-like crystals having a melting point of 101.5° to 102° C.

Elemental analysis values for C$_{15}$H$_{16}$O$_2$: Calculated (%): C 78.9 H 7.1; Found (%): C 78.8 H 7.2.

IR spectrum (KBr): An absorption attributed to the hydroxyl group at 3310 and 3200 cm$^{-1}$.

NMR spectrum (CDCl$_3$/DMSO-d$_6$=1:1): δppm 4.00 (2H, s, —CH$_2$—), 4.00–4.35 (2H, m, —OH x 2; disappeared in D$_2$O), 4.54 (2H, s, —CH$_2$OH), 4.62 (2H, s, —CH$_2$OH), 6.9–7.5 (8H, aromatic proton).

(C) Benzene (130 ml) and 52.3 g of thionyl chloride were added to 25 g of 4-(2-hydroxymethylbenzyl)benzyl alcohol, and the mixture was stirred at room temperature for 2.5 hours. The solvent was distilled off. The residue was dissolved in 100 ml of benzene and washed with water. The benzene layer was dried over anhydrous magnesium sulfate, and distilled off to afford 28 g of 4-chloromethyl-(2-chloromethylbenzyl)benzene as a pale yellow oily substance.

NMR spectrum (CDCl$_3$): δppm 4.07 (2H, s, —CH$_2$—), 4.40 (2H, s, —CH$_2$Cl), 4.43 (2H, s, —CH$_2$Cl), 6.9–7.3 (8H, aromatic proton).

(D) Potassium cyanide (15.58 g) was dissolved in 33 ml of water, and with stirring, 116 ml of ethanol was added. The mixture was heated to 70° to 75° C. Then, 26.42 g of 4-chloromethyl-(2-chloromethylbenzyl)benzene was added over the course of 15 minutes, and the mixture was heated under reflux for 4 hours with stirring. The reaction mixture was cooled, and the insoluble matter was removed by filtration. The solvent was distilled off. Benzene (100 ml) was added to the residue. The benzene solution was washed with water, and then with a saturated aqueous solution of sodium chloride. The benzene layer was dried over anhydrous magnesium sulfate, and the benzene was distilled off. To the residue was added 80 ml of ethanol, and 120 ml of a 20% aqueous solution of sodium hydroxide was added. The mixture was heated under reflux for 16 hours with stirring. After the reaction, the reaction mixture was cooled, and the solvent was distilled off. The residue was concentrated to half of its original volume. Water (100 ml) was added, and the mixture was washed with 50 ml of ether. The aqueous layer was acidified with 10% hydrochloric acid, and the precipitated solid was extracted with ethyl acetate. The ethyl acetate layer was washed with a saturated aqueous solution of sodium chloride and dried over anhydrous magnesium sulfate. The ethyl acetate was distilled off. The crystalline residue was recrystallized from a mixture of ethyl acetate and n-hexane to afford 22.0 g of 2-(4-carboxymethylbenzyl)phenylacetic acid as slightly yellow needle-like crystals having a melting point of 155° to 156° C.

REFERENTIAL EXAMPLE 3

Thallium trinitrate (0.49 g) was dissolved in 30 ml of methanol, and 0.5 ml of 70% perchloric acid was added. Under ice cooling, a solution of 0.13 g of 4-(2-acetylbenzyl)acetophenone in 0.8 ml of carbon tetrachloride was added. The mixture was then stirred at room temperature for 40 hours. The precipitated colorless crystalline insoluble matter was removed by filtration. To the filtrate was added three times its volume of water, and the mixture was extracted with chloroform. The chloroform layer was washed with a 10% aqueous solution of sodium bicarbonate, dried over anhydrous magnesium sulfate, and distilled off to remove the chloroform. The resulting brown oily substance was chromatographed over a silica gel column using chloroform as an eluent to afford 0.04 g of methyl 2-(4-methoxycarbonylmethylbenzyl)phenylacetate as a yellowish oily substance.

IR spectrum (neat): An absorption attributed to the ester group at 1730 cm$^{-1}$.

NMR spectrum (CCl$_4$): δppm 3.42 (4H, s, —CH$_2$COOCH$_3$×2), 3.49 (3H, s, —CH$_2$COOCH$_3$), 3.56 (3H, s, —CH$_2$COOCH$_3$), 3.84 (2H, s, —CH$_2$—), 6.9–7.2 (8H, aromatic proton).

REFERENTIAL EXAMPLE 4

In 20 ml of carbon tetrachloride was dissolved 0.50 g of 4-(2-acetylbenzyl)acetophenone, and 6.7 g of thallium trinitrate adsorbed to acidic montmorillonite (K-10) was added. The mixture was stirred at room temperature for 1 hour. The insoluble matter was removed by filtration. The carbon tetrachloride layer was washed with water, and dried over anhydrous magnesium sulfate. The carbon tetrachloride was distilled off to afford 0.48 g of methyl 2-(4-methoxycarbonylmethylbenzyl)phenylacetate as a yellowish oily substance.

The oily substance (0.43 g) was dissolved in 8 ml of ethanol, and 8 ml of a 20% aqueous solution of potassium hydroxide was added. The mixture was heated under reflux for 2 hours. The ethanol was distilled off, and the aqueous layer was washed with ether. The aqueous layer was then acidified with conc. hydrochloric acid, and the resulting colorless crystalline precipitate was collected by filtration, and recrystallized from ethyl acetate to afford 0.26 g of 2-(4-carboxymethylbenzyl)phenylacetic acid as a colorless crystalline powder having a melting point of 155° to 156° C.

Elemental analysis values for $C_{17}H_{16}O_4$: Calculated (%): C 71.8 H 5.7; Found (%): C 71.6 H 5.6.

IR spectrum (KBr): An absorption attributed to the carboxyl group at 3500–2300 cm$^{-1}$ and 1690 cm$^{-1}$.

NMR spectrum (CDCl$_3$/DMSO-d$_6$=10:1): δppm 3.53 (4H, s, —CH$_2$COOH×2), 3.97 (2H, s, —CH$_2$—), 6.9–7.3 (8H, aromatic proton), 10.25 (2H, bs, —COOH×2: disappeared in D$_2$O).

REFERENTIAL EXAMPLE 5

In 60 ml of carbon tetrachloride was dissolved 2.66 g of 4-(2-acetylbenzyl)propiophenone, and 36.0 g of thallium trinitrate adsorbed to acidic montmorillonite (K-10) was added. The mixture was heated under reflux for 1 hour. After the reaction, the reaction mixture was cooled, and then the insoluble matter was removed by filtration. The carbon tetrachloride layer was washed with water, dried over anhydrous magnesium sulfate, and distilled off to afford 2.68 g of methyl 2-[4-(1-methoxycarbonylethyl)benzyl]phenylacetate as a yellowish oily substance.

IR spectrum (neat): An absorption attributed to the ester group at 1730 cm$^{-1}$.

NMR spectrum (CCl$_4$):

| δ ppm | |
|---|---|
| 1.40 (3H, d, J = 7 Hz, —CHCH$_3$ with COOCH$_3$) | |
| 3.42 (1H, q, J = 7 Hz, —CHCH$_2$) with COOCH$_3$) | |
| 3.44 (2H, s, —CH$_2$COOCH$_3$), | |
| 3.46 (3H, s, —COOCH$_3$), | |
| 3.50 (3H, s, —COOCH$_3$), | |
| 4.92 (2H, s, —CH$_2$—), | |
| 6.3–7.2 (8H, aromatic proton). | |

The oily substance (2.54 g) was dissolved in 20 ml of ethanol, and 20 ml of a 20% aqueous solution of potassium hydroxide was added. The mixture was heated under reflux for 3 hours. The ethanol was distilled off. The aqueous layer was washed with ether, acidified with conc. hydrochloric acid, and extracted with ethyl acetate. The acetate layer was washed with water, dried over anhydrous magnesium sulfate, and distilled off. The resulting yellowish crystalline powder was recrystallized from benzene to afford 1.03 g of 2-[4-(1-carboxyethyl)benzyl]phenylacetic acid as a colorless crystalline powder having a melting point of 135° to 136° C.

The starting 4-(2-acetylbenzyl)propiophenone was prepared by the following method.

Anhydrous aluminum chloride (26.6 g) was suspended in 60 ml of carbon disulfide, and under ice cooling, a solution of 37.0 g of propionyl chloride in 60 ml of carbon disulfide was added dropwise. The mixture was stirred at room temperature for 30 minutes. The mixture was cooled with ice, and a solution of 8.4 g of o-benzylacetophenone in 60 ml of carbon disulfide was added dropwise. The mixture was stirred for 15 minutes under ice cooling. After the reaction, the reaction mixture was poured into a mixture of 300 ml of ice and 100 ml of conc. hydrochloric acid, and the carbon disulfide layer was separated. The aqueous layer was extracted with ether. The organic layers were combined, washed with a 10% aqueous solution of sodium bicarbonate and a saturated aqueous solution of sodium chloride, dried over anhydrous magnesium sulfate, and distilled off. The resulting pale yellow oily substance was chromatographed on a silica gel column using chloroform as an eluent to afford 9.4 g of 4-(2-acetylbenzyl)propiophenone as a pale yellow oily substance.

On standing for a while, this compound crystallized. Recrystallization from ethanol afforded yellowish prismatic crystals having a melting point of 56.5° to 57.5° C.

Elemental analysis values for $C_{18}H_{18}O_2$: Calculated (%): C 81.2 H 6.8; Found (%): C 81.0 H 6.8.

IR spectrum (KBr): An absorption attributed to the carbonyl group at 1675 cm$^{-1}$.

NMR spectrum (CDCl$_3$): δppm 1.01 (3H, t, J=7 Hz, —COCH$_2$CH$_3$), 2.29 (3H, s, —COCH$_3$), 2.32 (2H, q, J=7 Hz, —COCH$_2$CH$_3$), 4.19 (2H, s, —CH$_2$—), 6.85–7.80 (8H, aromatic proton).

In the same way as above, 4-(2-acetylbenzyl)acetophenone was prepared.

Form: yellow oily.

Elemental analysis values for $C_{17}H_{16}O_2$: Calculated (%): C 80.9 H 6.4; Found (%): C 80.8 H 6.4.

IR spectrum (neat): An absorption attributed to the carbonyl group at 1680 cm$^{-1}$.

NMR spectrum (CCl$_4$): δppm 2.46 (3H, s, —COCH$_3$), 2.50 (3H, s, —COCH$_3$), 4.32 (2H, s, —CH$_2$—), 7.05–8.91 (8H, aromatic proton).

What we claim is:

1. A dibenzo[a,d]cycloheptene derivative of the general formula $$R_1-\text{[benzene ring]}-Z-\text{[benzene ring]}-CH(R_2)COOR_3 \quad (I)$$

wherein $R_1$ represents a hydrogen atom, a halogen atom or a lower alkyl group, $R_2$ and $R_3$ each represent a hydrogen atom or a lower alkyl group, and Z represents a group of the formula $$-\underset{OR_3}{\overset{|}{C}}=CH- \quad \text{or} \quad -\underset{O}{\overset{\|}{C}}-CH_2-.$$

2. A process for producing a dibenzo[a,d]cycloheptene derivative of the general formula $$R_1-\text{[benzene ring]}-Z-\text{[benzene ring]}-CH(R_2)COOR_3 \quad (I)$$

wherein $R_1$ represents a hydrogen atom, a halogen atom or a lower alkyl group, $R_2$ and $R_3$ each represent a hydrogen atom or a lower alkyl group, and Z represents a group of the formula

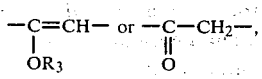

which comprises cyclizing a compound of the general formula

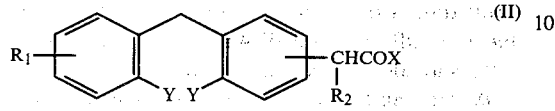

wherein $R_1$ and $R_2$ are as defined above, X represents a hydroxyl group or a halogen atom, one Y represents a group of the formula $-CH_2COX$, and the other Y represents a hydrogen atom, and hydrolyzing the cyclized product.

3. A process for producing a dibenzo[a,d]cycloheptene derivative of the general formula

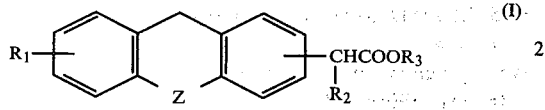

wherein $R_1$ represents a hydrogen atom, a halogen atom or a lower alkyl group, $R_2$ and $R_3$ each represent a hydrogen atom or a lower alkyl group, and Z represents a group of the formula

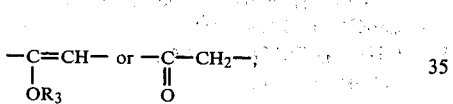

which comprises cyclizing a compound of the general formula

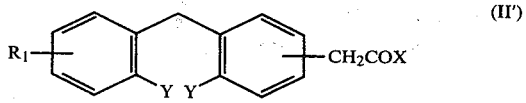

wherein $R_1$ is as defined above, X represents a hydroxyl group or a halogen atom, one Y represents a group of the formula $-CH_2COX$, and the other Y represents a hydrogen atom, hydrolyzing the cyclized product, to form a compound of the general formula

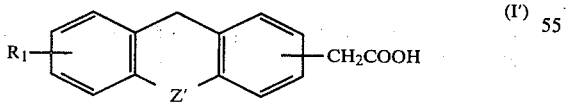

wherein $R_1$ is as defined above, and Z' represents a group of the formula

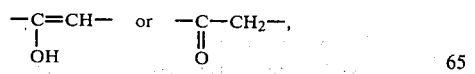

esterifying and enol-etherifying this compound to form a compound of the general formula

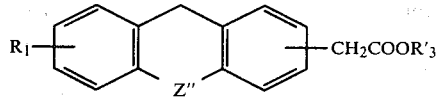

wherein $R_1$ is as defined above, $R'_3$ represents a lower alkyl group, and Z" represents a group of the formula

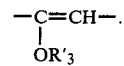

4. The process of claim 2 including the additional step of esterifying the cyclized product.

5. The process of claim 4 including the additional step of etherifying the enol group in the cyclized product.

6. The process of claim 2 including the additional step of etherifying the enol group in the cyclized product.

7. The process of claim 3 including the additional step of subjecting the compound of general formula (IV) to alkylation, dealkylation of the enol ether group and/or hydroysis.

8. A process for producing a dibenzo[a,d]cycloheptene derivative of the general formula

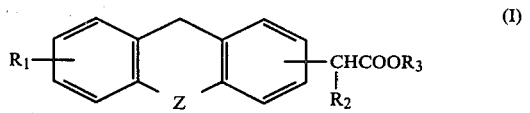

wherein $R_1$ represents a hydrogen atom, a halogen atom or a lower alkyl group, $R_2$ represents a lower alkyl group, $R_3$ represents a hydrogen atom or a lower alkyl group, and Z represents a group of the formula

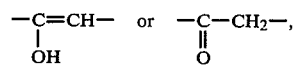

which comprises cyclizing a compound of the general formula

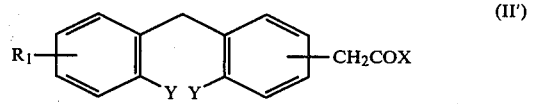

wherein $R_1$ is as defined above, X represents a hydroxyl group or a halogen atom, one Y represents a group of the formula $-CH_2COX$, and the other Y represents a hydrogen atom, hydrolyzing the cyclized product, to form a compound of the general formula

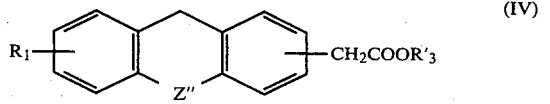

wherein $R_1$ is as defined above, $R'_3$ represents a lower alkyl group, and Z" represents a group of the formula

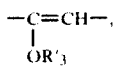

and subjecting the resulting compound to alkylation, dealkylation of the enol ether group, and/or hydrolysis.

9. The process of claim 2 wherein X is a hydroxyl group and the cyclization of the compound of formula (II) is carried out in the presence of a condensing agent selected from the group consisting of polyphosphoric acid, polyphosphoric acid esters and phosphoric anhydride.

10. The process of claim 2 wherein X is a halogen atom and the cyclization of the compound of formula (II) is carried out in the presence of a Friedel Crafts reaction catalyst selected from the group consisting of aluminum chloride, zinc chloride, stannous chloride, stannic chloride, titanium trichloride, boron trifluoride, antimony pentachloride and phosphoric anhydride.

11. The process of claim 3 wherein X is a hydroxyl group and the cyclization of the compound of formula (II') is carried out in the presence of a condensing agent selected from the group consisting of polyphosphoric acid, polyphosphoric acid esters and phosphoric anhydride.

12. The process of claim 3 wherein X is a halogen atom and the cyclization of the compound of formula (II') is carried out in the presence of a Friedel Crafts reaction catalyst selected from the group consisting of aluminum chloride, zinc chloride, stannous chloride, stannic chloride, titanium trichaloride, boron trifluoride, antimony pentachloride and phosphoric anhydride.

* * * * *